United States Patent
Chou et al.

(10) Patent No.: US 12,233,026 B2
(45) Date of Patent: Feb. 25, 2025

(54) GAS PERMEABLE SEALING MEMBER FOR DRUG CONTAINER AND METHODS OF ASSEMBLY

(71) Applicant: AMGEN INC., Thousand Oaks, CA (US)

(72) Inventors: Cheng-Chieh Chou, Los Angeles, CA (US); Mingda Eu, Oak Park, CA (US); Ren-Yo Forng, Potomac, MD (US); Wael Mismar, Redondo Beach, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 18/140,823

(22) Filed: Apr. 28, 2023

(65) Prior Publication Data
US 2023/0404850 A1    Dec. 21, 2023

Related U.S. Application Data

(63) Continuation of application No. 16/629,330, filed as application No. PCT/US2018/041567 on Jul. 11, 2018, now Pat. No. 11,672,733.
(Continued)

(51) Int. Cl.
*A61L 2/07* (2006.01)
*A61J 1/14* (2023.01)
(Continued)

(52) U.S. Cl.
CPC ............... *A61J 1/1406* (2013.01); *A61L 2/07* (2013.01); *A61L 2/206* (2013.01); *A61L 2/26* (2013.01); *A61L 2202/23* (2013.01)

(58) Field of Classification Search
CPC ... A61L 2/07; A61L 2/20; A61L 2/206; A61L 2/26; A61L 2202/23; A61J 1/1406
See application file for complete search history.

(56) References Cited

U.S. PATENT DOCUMENTS

| | | |
|---|---|---|
| 8,235,951 B2 | 8/2012 | Hund et al. |
| 2013/0270271 A1 | 10/2013 | Asai et al. |

(Continued)

FOREIGN PATENT DOCUMENTS

| | | |
|---|---|---|
| EP | 0239244 A1 | 9/1987 |
| FR | 2658082 A1 | 8/1991 |

(Continued)

OTHER PUBLICATIONS

Written Opinion for International Patent Application PCT/US2018/041567, dated Sep. 17, 2018.
(Continued)

*Primary Examiner* — Timothy C Cleveland
(74) *Attorney, Agent, or Firm* — MARSHALL, GERSTEIN & BORUN LLP

(57) ABSTRACT

Drug delivery devices, sealing members for containers housed within such drug delivery devices, and related methods of assembly are disclosed. The drug delivery device may include a housing, a container disposed in the housing and having an interior volume, a drug disposed in the interior volume, and a septum. The container may have an opening formed in an end surface and which communicates with the interior volume. The septum may include a proximal end inserted through the opening into the interior volume of the container. Additionally, the septum may include a distal end having a flange disposed outwardly of the proximal end and contacting the end surface of the container. At least an end portion of the flange may be made of a material that is permeable to a gaseous sterilizing agent.

6 Claims, 7 Drawing Sheets

Related U.S. Application Data

(60) Provisional application No. 62/535,777, filed on Jul. 21, 2017.

(51) Int. Cl.
 *A61L 2/20* (2006.01)
 *A61L 2/26* (2006.01)

(56) References Cited

U.S. PATENT DOCUMENTS

| | | | | |
|---|---|---|---|---|
| 2014/0220552 | A1* | 8/2014 | Moskowitz | G01N 33/86 |
| | | | | 435/307.1 |
| 2017/0296757 | A1 | 10/2017 | Maeda et al. | |
| 2019/0117880 | A1* | 4/2019 | Hirschel | A61M 5/31576 |

FOREIGN PATENT DOCUMENTS

| | | | |
|---|---|---|---|
| JP | 2004231216 A | 8/2004 | |
| JP | 2004533971 A | 11/2004 | |
| JP | 2008539025 A | 11/2008 | |
| JP | 2009-514634 A | 4/2009 | |
| WO | WO-02064439 A1 | 8/2002 | |
| WO | WO-2006116438 A2 | 11/2006 | |
| WO | WO-2008067467 A2 | 6/2008 | |
| WO | WO-2015084428 A1 | 6/2015 | |
| WO | WO-2016052037 A1 | 4/2016 | |
| WO | WO-2016/141082 A1 | 9/2016 | |
| WO | WO-2018151890 A1 | 8/2018 | |

OTHER PUBLICATIONS

International Search Report for International Patent Application PCT/US2018/041567, dated Sep. 17, 2018.
Japanese Patent Application No. 2019-566868, Decision of Rejection, mailed Jan. 17, 2023.
Non-final Office Action, U.S. Appl. No. 16/629,330, mailed Oct. 18, 2022.
English-language machine translation of JP2004231216A (Year: 2004).
Japanese Patent Application No. 2023-080592, Decision of Rejection, mailed Oct. 29, 2024.

\* cited by examiner

GAS PERMEABLE SEALING MEMBER FOR DRUG CONTAINER AND METHODS OF ASSEMBLY

CROSS-REFERENCE TO RELATED APPLICATION

This is a continuation of U.S. patent application Ser. No. 16/629,330, filed Jan. 8, 2020, which is a U.S. National Stage of PCT/US2018/041567, filed Jul. 11, 2018, which claims priority to U.S. Provisional Patent Application No. 62/535,777, filed Jul. 21, 2017. The entirety of the foregoing is expressly incorporated herein by reference for all purposes.

FIELD OF DISCLOSURE

The present disclosure generally relates to drug containers and, more particularly, to the assembly and sterilization of such containers within an injection.

BACKGROUND

Many drug containers or vials include an opening covered by a septum, which is also sometimes referred to as a stopper. The septum seals the drug within the container and usually is pierceable by a needle or other sharpened member to provide fluid communication with the drug. Conventional septa typically are constructed of a material with a very low gas and/or moisture permeability rate, to prevent the ingress of contaminants and leakage of the drug compositions. A risk of contamination nevertheless exits along the interface where the septum contacts the container.

Some drug containers are filled and closed with a septum under sterile or aseptic conditions, and thereafter stored within medical grade packaging until use by a patient or healthcare provider. Under such circumstances the risk of contamination of the interface between the septum and the container is low. In other scenarios, the drug container may be exposed to non-sterile or non-aseptic conditions during the filling procedure, thereby resulting in a risk of contamination at the interface between the septum and the container after the filling procedure. One such scenario is when a manufacturer installs a pre-filled drug container in a drug delivery device, such as a wearable injector or a pen-type injector, with the objective of creating a pre-filled and pre-loaded drug delivery device. Contamination can occur, for example, during the transport of the pre-filled drug container between the filling facility and the installation facility and/or within areas of the installation facility which are not operated under sterile or aseptic conditions. To address this contamination risk, oftentimes the manufacturer will subject the drug delivery device to a sterilization treatment near the end of the assembly process.

At this stage, however, the available sterilization treatments may be limited. This is because certain sterilization treatments can have deleterious effects on the drug within the container and/or the material used to construct the container. Radiation sterilization (e.g., gamma ray sterilization or electron beam sterilization) may cause oxidation of the drug and/or discoloration of the container glass. Though gaseous sterilization treatments such as ethylene oxide (EtO) and steam treatments may not cause damage to the drug or container material, in many cases they are not effective at killing bacteria or spores inoculated at the interface between a conventional septum and the container. Conventional septa have very low gas permeability rates and therefore will block the gaseous sterilization agent from reaching the interface between the septum and the container. It has been found that even extended ethylene oxide treatments (e.g., up to 30 hours) are not effective at sterilizing the interface between a conventional septum and the container. Furthermore, extended ethylene oxide treatments pose significant manufacturing challenges since they require long aeration cycles (e.g., 30-60 days) to extract residual ethylene oxide from the container and other components of the drug delivery device.

The present disclosure sets forth septa, container assemblies, drug delivery devices, and related methods of assembly embodying advantageous alternatives to existing versions of such devices and methods, and that may address one or more of the challenges or needs mentioned herein, as well as provide other benefits and advantages.

SUMMARY

One aspect of the present disclosure provides a drug delivery device including a housing, a container, a drug, and a septum. The container may be disposed in the housing and have an interior volume and an end surface. An opening may be formed in the end surface and communicate with the interior volume. The drug may be disposed in the interior volume of the container. The septum may include a proximal end and a distal end. The proximal end of the septum may be inserted through the opening into the interior volume of the container. The distal end of the septum may include a flange disposed outwardly of the proximal end and contacting the end surface of the container. At least an end portion of the flange may be made of a first material, and the first material may be permeable to a gaseous sterilizing agent. Furthermore, at least a portion of the distal end of the septum may be made of a second material.

Another aspect of the present disclosure provides a method of assembling a drug delivery device, the method including: (a) providing a container assembly including a container having an interior volume and an end surface, an opening being formed in the end surface and communicating with the interior volume, and a septum including a proximal end and a distal end, the proximal end being inserted through the opening into the interior volume of the container, the distal end including a flange disposed outwardly of the proximal end and contacting the end surface of the container, at least an end portion of the flange being made of a first material, where the first material is permeable to a gaseous sterilizing agent; (b) sterilizing the container assembly with a gaseous sterilizing agent such that the gaseous sterilizing agent diffuses through the first material to sterilize the end surface of the container; (c) filling the interior volume of the container with a drug; and (d) installing the container assembly in the drug delivery device.

Yet another aspect of the present disclosure provides container assembly including a container and a septum. The container may have a container having an interior volume and an end surface. An opening may be formed in the end surface and communicate with the interior volume. The septum may include a proximal end and a distal end. The proximal end of the septum may be insertable through the opening into the interior volume of the container. The distal end of the assembly may include a flange disposed outwardly of the proximal end. At least an end portion of the flange may be made of a first material, and the first material maybe permeable to a gaseous sterilizing agent. At least a portion of the distal end of the septum may be made of a second material.

An additional aspect of the present disclosure provides a container assembly including a container, a septum, and a ring-shaped sealing member. The container may have an interior volume and an end surface. An opening may be formed in the end surface and communicate with the interior volume. The septum may include a proximal end and a distal end. The proximal end of the septum may be insertable through the opening into the interior volume of the container. The distal end of the septum may include a flange disposed outwardly of the proximal end. The ring-shaped sealing member may be positioned between the flange and the end surface of the container. The ring-shaped sealing member may be made of a first material, and the first material maybe permeable to a gaseous sterilizing agent.

Another aspect of the present disclosure provides a septum for a drug container. The septum may include a longitudinal axis, a proximal end insertable into the drug container, and a distal end including a flange disposed radially outwardly of the proximal end. The flange may include an outer peripheral surface and a proximally facing surface. At least an end portion of the flange may be made of a first material. The first material may be permeable to a gaseous sterilizing agent such that the gaseous sterilizing agent is permitted to diffuse through the first material between the outer peripheral surface of the flange and the proximally facing surface of the flange. At least a portion of the distal end of the septum may be made of a second material.

Yet another aspect of the present disclosure provides a drug delivery device including a housing, a container, a drug, and a septum. The container may be disposed in the housing and have an interior volume and an end surface. An opening may be formed in the end surface and communicate with the interior volume. The drug may be disposed in the interior volume of the container. The septum may include a proximal end and a distal end. The proximal end of the septum may be inserted through the opening into the interior volume of the container. The distal end of the septum may include a flange disposed outwardly of the proximal end and contacting the end surface of the container. Furthermore, an entirety of the septum may be made of a material that is permeable to a gaseous sterilizing agent.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

The present disclosure generally concerns protecting a drug stored in a container (e.g., a vial or ampule) from microbes and other contaminants. Sealing close an opening of such containers is often accomplished with a septum, or what is referred to by some as a stopper. The septum may include a proximal or bottom end that is inserted through the opening into the container, and an enlarged distal or top end that abuts against an end surface or rim of the container. The engagement of the enlarged distal end of the septum and the end surface of the container may inhibit the ingress of contaminants. In addition to providing a contaminant barrier, the presently disclosed septa advantageously facilitate the sterilization of an interface between the septum and the container during manufacturing. This aspect of the presently disclosed septa is facilitated by constructing the septum, at least partially, of a material that is permeable to gaseous sterilizing agent(s) such as ethylene oxide (EtO) and/or steam, for example. This permeability may allow a gaseous sterilizing agent to diffuse through the septum and sterilize the interface between the septum and the container. Other portions of the septum may be constructed of a different material which is less permeable, or even non-permeable, to the gaseous sterilizing agent, thereby resulting in a composite septum made of at least two different materials. Also, as described below, the embodiments of the septum according to the present disclosure advantageously permit a drug container, which may or may not be pre-filled, to be installed or assembled in a drug delivery device under non-sterile or non-aseptic conditions, and then later subjected to a gaseous sterilization treatment without damaging the drug stored in the container. Further disclosed is a sealing member such as a gasket which is separate from the septum and positioned between the septum and the end surface of the container. The sealing member may be constructed of a material that is permeable to a gaseous sterilizing agent to provide a diffusion pathway for a gaseous sterilizing agent to eliminate or reduce contaminants existing at the end surface of the container.

Each of the foregoing components and methods of assembling a drug delivery device including these components will now be described in more detail.

Before describing various embodiments of a septum constructed in accordance with principles of the present disclosure, a general overview of a drug delivery device is provided with reference to FIG. 1, in which the below-described septum embodiments can be implemented.

Figure 1:
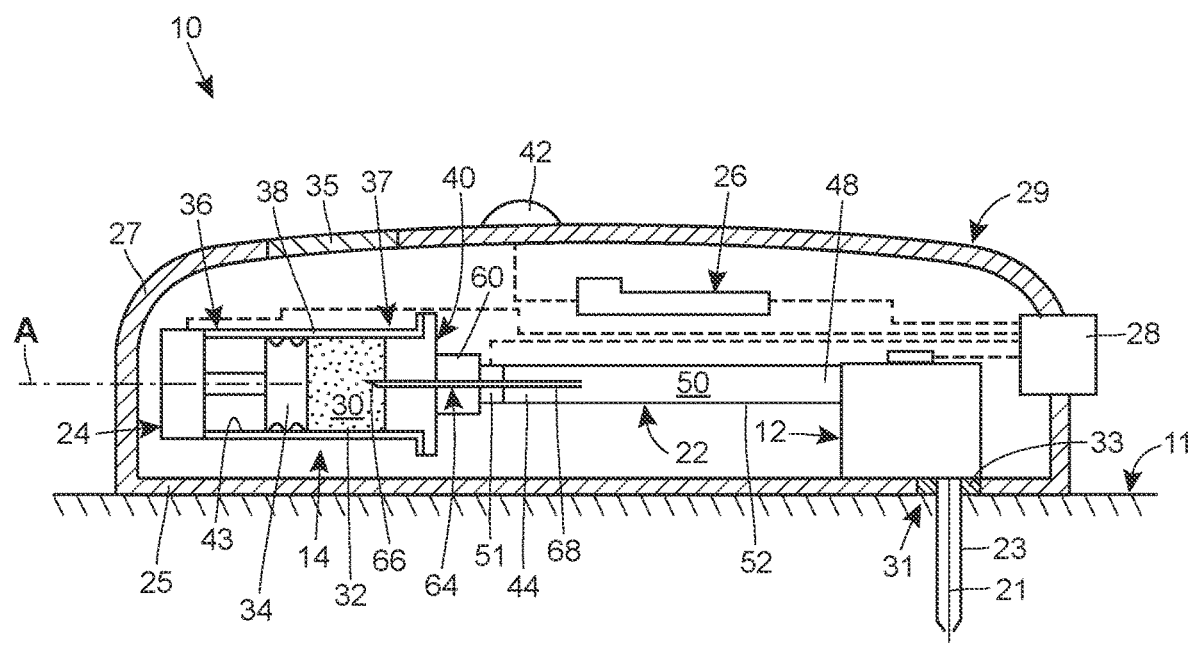
FIG. 1 illustrates a schematic cross-sectional view of an embodiment of a drug delivery device in accordance with principles of the present disclosure.

FIG. 1 illustrates an embodiment of a drug delivery device 10 which may be operated to subcutaneously or transdermally deliver a drug to a patient. In the illustrated embodiment, the drug delivery device 10 is configured as a wearable drug delivery device, such as an on-body injector or an ambulatory infusion pump, which is releasably attached to the patient's tissue 11 (e.g., the patient's skin). In other embodiments (not illustrated), the drug delivery device 10 may be configured as a pen-type injector, such as an auto-injector or injection pen, which is temporarily held against the patient's tissue 11 over the course of the injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include an insertion mechanism 12, a container 14, a fluid pathway assembly 22, a drive mechanism 24, and a controller 26, each of which may be disposed within an interior space of a main housing 29. An actuator 28 (e.g., a user-depressible button, touchscreen, microphone, etc.) may protrude through or otherwise be disposed at an exterior surface of the housing 29 and may be configured to initiate operation of the drug delivery device 10 by activating, via mechanical and/or electrical means (shown in dotted lines in FIG. 1), the insertion mechanism 12, the fluid pathway assembly 22, the drive mechanism 24, the controller 26, and/or other mechanisms and/or electronics. In embodiments where the actuator 28 is a button that is depressed or otherwise physically moved by a user or patient, the actuator 28 may be configured to exert a motive force needed to activate the insertion mechanism 12, the fluid pathway assembly 22, the drive assembly 24, the controller 26, and/or other mechanisms. In such embodiments, the actuator 28 may be physically connected to, either directly or indirectly via a mechanical linkage, the insertion mechanism 12, the drive mechanism 24, the fluid pathway assembly 22, and/or other mechanisms such that manually depressing or otherwise interacting with the actuator 28 supplies the motive force necessary to activate the insertion mechanism 12, the drive mechanism 24, the fluid pathway assembly 22, and/or other mechanisms. For example, in some embodiments, manually depressing the actuator 28 may cause the fluid pathway assembly 22 to move towards the stationary container 14, or cause the container 14 to move towards the stationary fluid pathway assembly 22, and thereby cause a container access needle to penetrate through a seal member into a reservoir or interior volume of the container 14. Additionally or alternatively, the actuator 28 may operate as an input device that transmits an electrical and/or mechanical signal to the controller 26, which in turn may execute programmable instructions to control operation of the insertion mechanism 12, the drive mechanism 24, the fluid pathway assembly 22, and/or other mechanisms. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 28 and which, in response to an electrical control signal received from the controller 26, exerts the motive force needed to activate the insertion mechanism 12, the drive mechanism 24, the fluid pathway assembly 22, and/or other mechanisms.

Still referring to FIG. 1, the housing 29 may include a bottom wall 25 configured to be releasably attached (e.g., adhered with an adhesive) to the patient's tissue 11, and a top wall 27 including one or more visual indicators 42 (e.g., lights, graphical displays, etc.) and/or a window 35 for viewing the container 14 and the drug 32 contained therein. The one or more visual indicators 42 may be used to communicate information to the user about the operational state of the drug delivery device 10 and/or the condition of the drug 32. An opening 31 may be formed in the bottom wall 25, and optionally a pierceable sterile barrier 33 may extend across the opening 31 to seal the interior of the housing 29 prior to use. In some embodiments, the pierceable sterile barrier 33 may be omitted, and instead a removable sealing member (not illustrated) may cover and seal close the opening 31 prior to use.

More particularly with respect to the window 35, this element may be constructed of a transparent or semi-transparent material and generally aligned with the container 14, so as to allow a patient or user of the drug delivery device 10 to inspect the drug 32 within the container 14 and/or confirm dose completion. Suitable materials for constructing the window 35 include, but are not limited to, glass and plastic. Since the window 35 is located on the exterior of the drug delivery device 10, it may expose the drug 32 to ambient light such as sunlight. Some drugs may be sensitive to certain wavelengths of light and undergo undesirable molecular changes when exposed to light. For example, some drugs may be sensitive to wavelengths of light in the ultraviolet (UV) range, the visible range, and/or the infrared range. To protect drugs that are primarily sensitive to light in the UV range and/or the infrared range, a dark tint may be added to the window 35 and/or the window 35 may be dimensioned to cover a relatively small surface area of the housing 29. For drugs that are primarily sensitive to light in the visible range, it may not be necessary to add a dark tint to the window 35 and/or shrink the size of the window 35. Instead, the window 35 may be constructed with a polarized filter. In some embodiments, the polarized filter may be a film or other coating that is applied to the window 35. In other embodiments, the polarized filter may be integrated directly into the material of window 35. The polarized filter may allow for viewing and inspection of the drug 32 within the container 14, while filtering out up to and including approximately (e.g., ±10%) 50% of light in the visible range. In some embodiments, the portion of visible light filtered out by the window 35 may fall in a range between approximately (e.g., ±10%) 0-50%, or 10-50%, or 20-50%, or 25-50%, or 0-40%, or 0-30%, or 0-25%, depending on the photosensitivity of the drug 32 and/or the typical eye strength of the patient population of the drug 32, among other considerations. Adding the polarized filter to the window 35 in lieu adding a dark tint to the window 35 and/or shrinking the size of the window 35 advantageously protects the drug 35 from light in the visible range without substantially compromising the ability of the patient or user of the drug delivery device 10 to inspect the drug 32 prior to and/or during the injection.

After the bottom wall 25 of the housing 29 is attached to the patient's tissue 13, the insertion mechanism 12 may be activated to move a delivery member from a retracted position within the housing 29 to a deployed position extending outside of the housing 29. In the present embodiment, this involves the insertion mechanism 12 inserting a trocar 21 and a hollow cannula 23 surrounding the trocar 21 through the pierceable sterile barrier 33 and into the patient's tissue 11, as illustrated in FIG. 1. Immediately or shortly thereafter, the insertion mechanism 12 may automatically retract the trocar 21, leaving the distal open end of the cannula 23 inside the patient for subcutaneous delivery of the drug 32. The trocar 21 may be solid and have a sharpened end for piercing the patient's skin 11. Furthermore, the trocar 21 may be made of a material that is more rigid than the cannula 23. In some embodiments, the trocar 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient. In other embodiments (not illustrated), the trocar 21 and cannula 23 may be omitted, and instead the insertion mechanism 12 may insert only a rigid, hollow needle into the patient for subcutaneous delivery of the drug 32.

In some embodiments, the insertion mechanism 12 may include one or more springs (e.g., coil springs, torsion springs, etc.) initially retained in an energized state, and which are released upon depression of the actuator 28 in order to insert the trocar 21 and cannula 23, or hollow needle, into the patient. Furthermore, retraction of the trocar 21 may be achieved by the automatic release of another spring after the trocar 21 and cannula 23 have been inserted into the patient. Other power sources for insertion and/or retraction are possible, including, for example, an electric motor, a hydraulic or pneumatic pump, or a canister that releases a pressurized gas or pressurized liquid to provide actuation energy.

With continued reference to FIG. 1, the container 14, which in some contexts may be referred to as a primary container, may include a wall 38 defining an interior volume 30 or reservoir that contains the drug 32. In some embodiments, the interior volume 30 may be pre-filled with the drug 32 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the housing 29 such that the container 14 can move relative to the housing 29 during operation of the drug delivery device 10. The container 14 may have an elongate, barrel-like or cylindrical shape extending along a longitudinal axis A. In embodiments where the drug delivery device 10 is configured as an on-body injector, the longitudinal axis A of the container 14 may be perpendicular or substantially perpendicular, or otherwise non-parallel, to a direction in which the insertion mechanism 12 inserts a delivery member such as the cannula 23 into the patient. This configuration may allow the on-body injector to have a generally planar, low profile shape that can be worn by the patient without impeding the patient's movement. Initially, a stopper 34 or other piston member may be positioned in the interior volume 30 at a proximal end 36 of the container 14. The stopper 34 may sealingly and slidably engage an inner surface 43 of the wall 38 of the container 14, and may be movable relative to the wall 38 of the container 14.

The volume of the drug 32 contained in the container 14 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL. The interior volume 30 of the container 14 may be completely or partially filled with the drug 32. The drug 32 may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive mechanism 24 may push the stopper 34 along the longitudinal axis A from the proximal end 36 of the container 14 to the distal end 37 of the container 14 in order to expel the drug 32 from the container 14. In some embodiments, the drive mechanism 24 may include one or more springs (e.g., coil springs, torsion springs, etc.) initially retained in an energized state, and which are released upon depression of the actuator 28. Following their release, the spring(s) may expand and move the stopper 34 through the interior volume 30 along the longitudinal axis A from the proximal end 36 of the container 14 to the distal end 37 of the container 14. In other embodiments, the drive mechanism 24 may include an electric motor (not illustrated) which rotates a gear mechanism, including for example one or more sprocket gears, to cause axial motion of the stopper 34 through the interior volume 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy.

At the distal end 37 of the container 14, an opening 45 (see FIG. 2A) may be formed in a distal end surface 72 (see FIG. 2A) of the wall 38. At least prior to operation of the drug delivery device 10, the opening 45 may be covered and sealed closed by a septum 40 connected to the distal end 37 of the container 14. Generally, the septum 40 may be configured to selectively permit access to the interior volume 30. During operation, the septum 40 may be physically altered to permit fluid communication with the drug 32 in the interior volume 30. As discussed below, the septum 40 may be constructed of a flexible or elastically deformable material such as rubber, for example, which is capable of being penetrated or pierced by a point or sharpened end 66 of a container access needle 64 mounted on the fluid pathway assembly 22. In some embodiments, the septum 40 may be clamped or otherwise secured to the distal end surface 72 by a fastener 94 (see FIG. 2B) and/or adhered directly to the distal end surface 72.

Still referring to FIG. 1, the fluid pathway assembly 22 may be configured to establish fluid communication between the container 14 and the insertion mechanism 12 via a sterile fluid flow path during operation of the drug delivery device 10. Prior to use of the drug delivery device 10, the fluid pathway assembly 22 may not be in fluid communication with the container 14. During setup of the drug delivery device 10, or during the initial stages of operation of the drug delivery device 10 prior to drug delivery, the user may manually, or the drug delivery device 10 may automatically, enable, connect, or open the necessary connections to establish fluid communication between the container 14 and the fluid pathway assembly 22. Subsequently, the drive mechanism 24 may move the stopper 34 in the distal direction to force the drug 32 stored in the container 14 through the sterile fluid flow path of the fluid pathway assembly 22 and into the cannula 23 or needle of the insertion mechanism 12 for subcutaneous delivery to the patient.

In some embodiments, the fluid pathway assembly 22 may be rigidly connected to the housing 29 such that the fluid pathway assembly 22 cannot move relative to the housing; whereas, in other embodiments, the fluid pathway assembly 22 may be slidably connected to the housing 29 such that the fluid pathway assembly 22 can move relative to the housing 29 during operation of the drug delivery device 10.

The fluid pathway assembly 22 may include a first end 44 having an opening, a second end 48 fluidly connected to the insertion mechanism 12, and a fluid passage 50 extending between the first end 44 and the second end 48. The fluid passage 50 may be sterilized, and may be partially or entirely made of a flexible tubing 52. Initially, there may be slack in the flexible tubing 52 to allow the fluid pathway assembly 22 to move relative to the housing 29 and/or to allow components of the insertion mechanism 12 to which the fluid pathway assembly 22 is attached to move relative to the housing 29. In some embodiments, the fluid passage 50 may include a rigid fluid restrictor element (not illustrated) in addition to the flexible tubing 52. The fluid restrictor element may have a smaller inner diameter than that of the flexible tubing 52 in order to regulate the flow rate of the drug 32 as it passes through the fluid pathway assembly 22. Furthermore, the fluid restrictor element may be made of a more rigid material than the flexible tubing 52. For example, the fluid restrictor element made be made of metal, whereas the flexible tubing 52 may be made of a polymeric material such as plastic.

Prior to operation of the drug delivery device 10, the opening at the first end 44 of the fluid pathway assembly 22 may be covered and initially sealed closed by a seal member 60 (e.g., a septum) which is connected to the first end 44 of the fluid pathway assembly 22. In a general sense, the seal member 60 may be configured to control access to the fluid passage 50. During operation of the device 10, in some embodiments the seal member 60 may be physically altered to permit fluid communication with the fluid passage 50. The seal member 60 may be axially aligned with the septum 40 such that a proximal exterior end surface of the seal member 60 faces a distal end surface of the septum 40. In some embodiments, both the septum 40 and the seal member 60 may be axially aligned along the longitudinal axis A of the container 14 when installed in the drug delivery device 10. Additionally, in some embodiments the container access needle 64 may be axially aligned with the longitudinal axis A of the container 14.

Still referring to FIG. 1, the container access needle 64, which may be rigid and hollow, may extend from the first end 44 of the fluid pathway assembly 22. The first end 66 of the container access needle 64, which may be sharpened, may protrude from the first end 44 of the fluid pathway assembly 22; and a second end 68 of the container access needle 64 may be in fluid communication with the fluid passage 50. The first end 66 of the container access needle 64 may have an opening that is initially covered and sealed by, or embedded within, the seal member 60. In some embodiments, the fluid pathway assembly 22 may include a mounting member 51 or connection hub for rigidly connecting the container access needle 64 to the remainder of the fluid pathway assembly 22, so that the container access needle 64 cannot move relative to the fluid pathway assembly 22, and so that, to the extent that the fluid pathway assembly 22 moves relative to the housing 29, the fluid pathway assembly 22 and the container access needle 64 move together jointly as a single unit relative to the housing 29. Furthermore, the seal member 60 may be mounted on the container access needle 64 so that the seal member 60 is connected to the first end 44 of the fluid pathway assembly 22 by way of the container access needle 64. Furthermore, in such embodiments, the seal member 60 may be constructed as a deformable septum, or as a collapsible or rigid sleeve defining a sterile interior chamber, enclosing the exposed first end 66 of the container access needle 64.

Furthermore, where appropriate, any of the above-described sub-assemblies, mechanisms, components, features, functionalities, methods of manufacture, methods of use, and other aspects of the drug delivery device 10 may be replaced with and/or combined with any of the sub-assemblies, mechanisms, components, features, functionalities, methods of manufacture, methods of use, and other aspects of the drug delivery devices described in some or all of the following documents: U.S. Pat. No. 9,061,097; U.S. Patent Application Publication No. 2017/0124284; U.S. Patent Application Publication No. 2017/0119969; U.S. Patent Application Publication No. 2017/0098058; U.S. Patent Application Publication No. 2017/0124285; U.S. Patent Application Publication No. 2017/0103186; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; U.S. Provisional Patent Application No. 62/468,190 entitled "INSERTION MECHANISM AND METHOD OF INSERTING A NEEDLE OF A DRUG DELIVERY DEVICE"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE"; International Patent Application No. PCT/US2017/017627 entitled "DRUG DELIVERY DEVICE, METHOD OF MANUFACTURE, AND METHOD OF USE"; and International Patent Application No. PCT/US2017/026524 entitled "DRUG DELIVERY DEVICE, METHOD OF MANUFACTURE, AND METHOD OF USE".

Figure 2A:
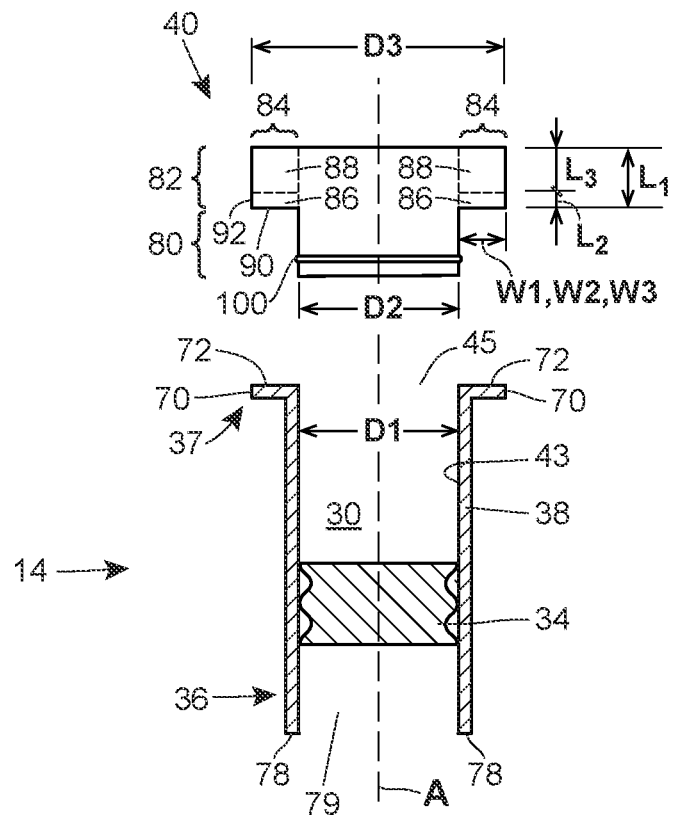
FIG. 2A depicts an exploded view of a container assembly depicted in FIG. 1, with the container and stopper being illustrated in cross-section.
Figure 2B:
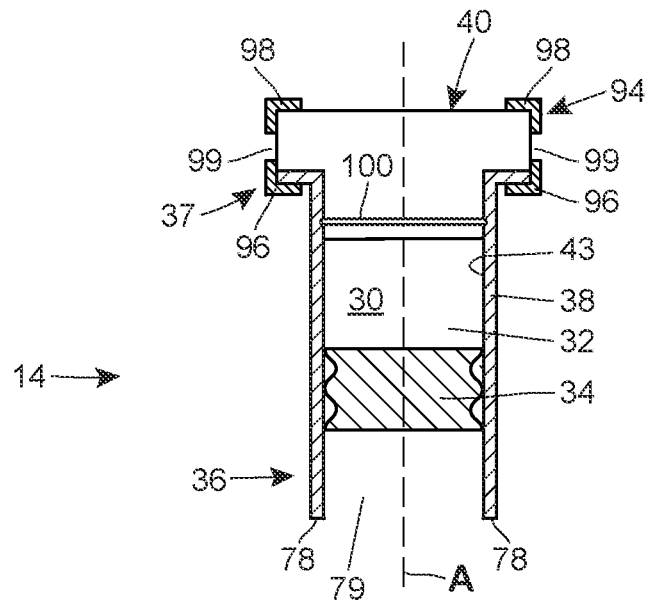
FIG. 2B illustrates an assembled view of the container assembly illustrated in FIG. 2A, with the container, the stopper, and the fastener being shown in cross-section.

Turning to FIGS. 2A and 2B, illustrated is an enlarged view of the container assembly of the drug delivery device 10. The container assembly includes the container 14, the septum 40, and the stopper 34. The container 14 may have a generally cylindrical shape with an inner diameter D1. At the distal end 37 of the container 14, the wall 38 may protrude radially outwardly to define a container flange 70. The container flange 70 may extend partially or entirely around a circumference of the distal end 37 of the container 14. The container flange 70 may define a distal end surface 72 of the container 14, which is perpendicular or otherwise non-parallel to the longitudinal axis A of the container 14 and generally faces in a distal direction. The opening 45 may be formed in the distal end surface 72 and communicate with the interior volume 30 of the container 14. In some embodiments, the container flange 70 may be omitted such the distal end surface 72 does not project radially outwardly of a remainder of the container 14. The wall 38 at the proximal end 36 of the container 14 may include a proximal end surface 78, which is perpendicular or otherwise non-parallel to the longitudinal axis A of the container 14 and generally faces in a proximal direction. An opening 79 may be formed in the proximal end surface 78 and communicate with the interior volume 30. The stopper 34 may inserted through the opening 79 into the interior volume 30 after the container 14 has been filled with the drug 32. The container 14 may be constructed of glass, plastic, or any other suitably inert material which may not chemically interact with the drug 32.

Referring still to FIGS. 2A and 2B, the septum 40 may be centrally aligned with the longitudinal axis A of the container 14 when the septum 40 is inserted into the container 14 such that the septum 40 and the container 14 share the same longitudinal axis A. The septum 40 may be divided by an imaginary plane perpendicular to the longitudinal axis A into a proximal (or bottom) end 80 and a distal (or top) end 82. The proximal end 80 and the distal end 82 may each possess a cylindrical shape and have outer diameters D2 and D3, respectively, as seen in FIG. 2A. The distal end 82 may be enlarged relative to the proximal end 80, such that the outer diameter D3 (or other outer dimension) of the distal end 82 is larger than an outer diameter D2 (or other outer dimension) of the proximal end 80. A flange 84 of the septum 40 is defined by an outer peripheral (e.g., circumferential) portion of the distal end 82 of the septum 40 that is disposed radially outwardly of the proximal end 80 of the septum 40. The flange 84 may have a length L1 parallel to the longitudinal axis A and a width W1 perpendicular to the longitudinal axis A.

The flange 84 of the septum 40 may include a proximal end portion 86 and a distal end portion 88, each of which has its boundary denoted by dashed lines in FIG. 2A. The proximal end portion 86 may have a length L2 parallel to the longitudinal axis A and a width W2 perpendicular to the longitudinal axis A. Similarly, the distal end portion 88 may possess a length L3 parallel to the longitudinal axis A and a width W3 perpendicular to the longitudinal axis A. Each of the lengths L2 and L3 may be less than the overall length L1 of the flange 84; whereas each of the widths W2 and W3 may be equal to the overall width W1 of the flange 84a. The proximal end portion 86 of the flange 84 may include: a proximal end surface 90 which is perpendicular or otherwise non-parallel to the longitudinal axis A and generally faces in the proximal direction; and an outer peripheral (e.g., circumferential) surface 92 which may be centered about and/or parallel to the longitudinal axis A.

Referring to FIG. 2B, when the septum 40 is attached to the container 14, the proximal end 80 of the septum 40 may be inserted through the opening 45 into the interior volume 30 and the proximal end surface 90 of the proximal end portion 86 of the flange 84 may directly contact and sealingly engage the distal end surface 72 of the container 14. In some embodiments, each of the proximal end surface 90 and the distal end surface 72 may be planar such that they flushly engage each other. In other embodiments, flush engagement may be achieved by configuring the proximal end surface 90 and the distal end surface 72 with mating curvatures, such as one being convex and the other being concave.

Referring to FIG. 2B, a fastener 94 may be configured to hold the septum 40 against the container 14. In some embodiments, the fastener 94 may take the form of a crimp ring that is applied to the container 14 and septum 40 with a crimping tool. As shown in FIG. 2B, the fastener 94 may include radially inwardly extending flanges 96 and 98 that abut against, respectively, a proximally facing surface of the container flange 70 (or other exterior surface of the wall 38 of the container 14) and a distally facing end surface of the distal end 82 of the septum 40, in order to clamp or press the proximal end surface 90 of the flange 84 of the septum 40 tightly against the distal end surface 72 of the container 70. The clamping force provided by the fastener 94 may help ensure an air-tight and/or fluid-tight seal between the proximal end surface 90 of the flange 84 of the septum 40 and the distal end surface 72 of the container 70. As described in more detail below, in some embodiments, the fastener 94 may be made of a material that is permeable to a gaseous sterilizing agent such as EtO and/or steam.

Figure 3A:
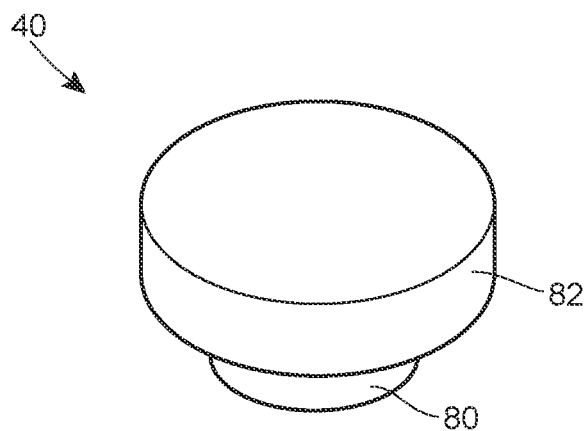
FIG. 3A is a top perspective view of a septum depicted in FIGS. 1-2B.
Figure 3B:
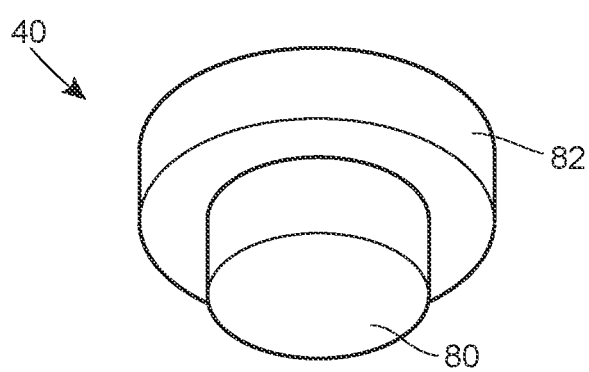
FIG. 3B is a bottom perspective view of the septum depicted in FIG. 3A.

Still referring to FIG. 2B, the proximal end 80 of the septum 40 may include one or more radially outwardly protruding annular ribs 100 for sealingly engaging the inner surface 43 of the wall 38 of the container 14. The annular ribs 100 may provide a secondary barrier to prevent the ingress contaminants that breach the seal between the proximal end surface 90 of the flange 84 of the septum 40 and the distal end surface 72 of the container 70. Here, the outer diameter D2 of the proximal end 80 of the septum 40 may be equal to or less than inner diameter D1 of the container 14. In other embodiments, the annular ribs 100 may be omitted (see FIGS. 3A and 3B), and the outer diameter D2 of the proximal end 80 of the septum 40 may be slightly larger than the inner diameter D1 of the container 14 to provide a tight fit and seal. In still further embodiments, the annular ribs 100 may be omitted and the outer diameter D2 of the proximal end 80 of the septum 40 may be smaller than the inner diameter D1 of the container 14, such that there is not a seal formed therebetween.

Prior to placing the drug delivery device 10 in its final packaging or sealing close the interior space of the housing 29, it may be advantageous to subject the fully or partially assembled drug delivery device 10 to a sterilization treatment in order to reduce or eliminate microbes or other contaminants, airborne or stationary, within or on the housing 29. Such a sterilization treatment may be essential if any of the earlier steps of assembling the drug delivery device 10 occurred in a non-sterile or non-aseptic environment. Before its installation in the drug delivery device 10, the container 14 may be filled and covered with the septum 40 by a drug manufacturer in sterile or aseptic environment, where there is little risk of contamination. However, if the container 14 is shipped to a manufacturer of the drug delivery device 10 and/or installed by the device manufacturer under non-sterile or non-aseptic conditions, a risk exists that contaminants may breach the seal between the septum 40 and the container 14 and become attached between the flange 84 of the septum 40 and the distal end surface 72 of the container 14, or even potentially contaminate the drug 32. Though radiation sterilization (e.g., gamma ray sterilization or electron beam sterilization) might be able to sterilize contaminants at the interface between the flange 84 of the septum 40 and the container 14, radiation sterilization after installation of the pre-filled container 14 in the drug delivery device 10 may not be feasible due to the potential for the high energy sterilization beams to damage to the drug 32 in the container 14. Gaseous sterilization treatments may not harm the drug 32, but may be unable to penetrate the seal between the flange 84 of the septum 40 and the container 14 to sterilize the proximal end surface 90 and/or the distal end surface 72.

To address this issue, the septum 40, the fastener 94, and/or other components associated with the container 14 may be constructed, partially or entirely, of a material that is permeable to a gaseous sterilizing agent including, but not limited to, EtO and/or steam. This material may provide a diffusion pathway for molecules of the gaseous sterilizing agent to diffuse through at least the septum 40 and sterilize one or more surfaces, such as the proximal end surface 90 and/or the distal end surface 72, that otherwise would be not feasible to sterilize due to the inability of the gaseous sterilizing agent to penetrate the seal formed at the interface between the septum 40 and the container 14.

FIGS. 4-7 illustrate four versions of the above-described septum 40, each having a different material composition but each having the same dimensional and geometric characteristics as those shown in FIGS. 1-3B. Each version of the septa 40 is appended with a respective one of the suffixes: "a", "b", "c", or "d". Common to all versions of the septum 40a, 40b, 40c, and 40d illustrated in FIGS. 4-7 is that at least the proximal end portion 86 of the flange 84, including its proximal end surface 90 and outer peripheral surface 92, is made of a first material that is permeable to a gaseous sterilizing agent, including at least one of EtO or steam. Accordingly, each of the septa 40a-d has at least one diffusive pathway for the gaseous sterilizing agent extending between the proximal end surface 90 and outer peripheral surface 92. Thus, during a sterilization procedure in which a partially or fully assembled drug delivery device 10 is exposed to the gaseous sterilizing agent, the gaseous sterilizing agent can enter the septum 40 through at least the outer peripheral surface 92 and exit the septum 40 through at least the proximal end surface 90 to sterilize the interface between the septum 40 and the container 40, including at least the proximal end surface 90 of the flange 84 and the distal end surface 72 of the container 14. Other diffusive pathways through the septum 40 may also be possible, depending on the portion(s) of the septum 40 constructed of the first material that is permeable to the gaseous sterilizing agent. The rate at which the gaseous sterilizing agent diffuses through each of the septa 40a, 40b, 40c, and 40d may depend upon the proportion of the septum made of the first material. Also, although the one or more annular ribs 100 are omitted from FIGS. 4-7, any of the embodiments of the septum 40a, 40b, 40c, and 40d may include the one or more annular ribs 100.

Figure 4:
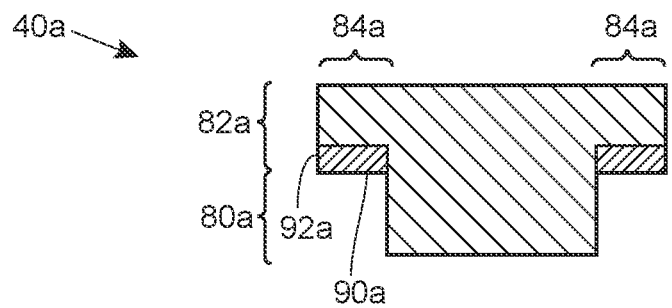
FIG. 4 is a cross-sectional view of an embodiment of a septum constructed in accordance with principles of the present disclosure.

Looking to FIG. 4, illustrated is an embodiment of the septum 40a in which only the proximal end portion 86a of the flange 84a may be made of a first material that is permeable to a gaseous sterilizing agent, including at least one of EtO or steam. As such, only a ring-shaped portion of the septum 40a defined by the proximal end portion 86a of the flange 84a may be made of the first material that is permeable to the gaseous sterilizing agent. The remainder of the septum 40a, including the distal end portion 88 of the flange 84 and the proximal end 80a of the septum 40a, may be made of a second material that is less permeable to the gaseous sterilizing agent than the first material. In some embodiments the second material may be substantially or completely impermeable to the gaseous sterilizing agent. Furthermore, in some embodiments of the septum 40a, the gaseous sterilizing agent may enter the septum 40a only through the outer peripheral surface 92a of the flange 84a and exits the septum 40a primarily or only through the proximal end surface 90a of the flange 84. This may be useful in preventing the gaseous sterilizing agent from entering the interior volume 30 of the container 14 and interacting with the drug 32.

Figure 5:
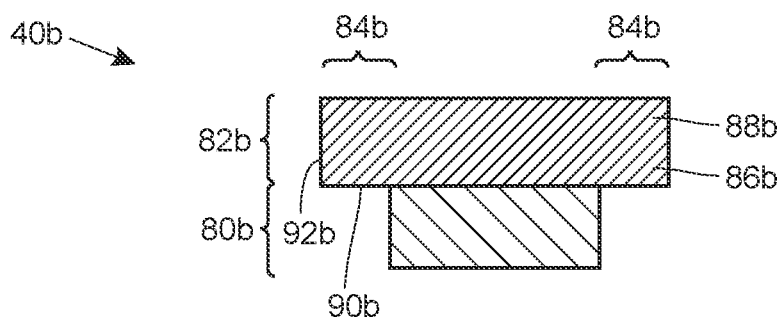
FIG. 5 is a cross-sectional view of another embodiment of a septum constructed in accordance with principles of the present disclosure.

FIG. 5 illustrates another embodiment of the septum 40b, where the gaseous sterilizing agent may have additional ways to enter the septum 40b, including through the entire outer peripheral surface of the distal end 82b of the septum 40b as well as the entire distal end surface of the septum 40b. This scheme may be achieved by constructing the distal end 82b of the septum 40b entirely of the first material that is permeable to the gaseous sterilizing agent, including at least one of EtO or steam. The proximal end 80b of the septum 40b may made entirely of the second material which is less permeable to the gaseous sterilizing agent than the first material. In some embodiments the second material may be substantially or completely impermeable to the gaseous sterilizing agent. Similar to the septum 40a, the gaseous sterilizing agent may exit the septum 40b primarily or only through the proximal end surface 90b of the flange 84b. In some embodiments, the first material of the septum 40b may be made of a polybutadiene rubber, and the second material of the septum 40b may be made of a chlorobutyl rubber.

Figure 6:
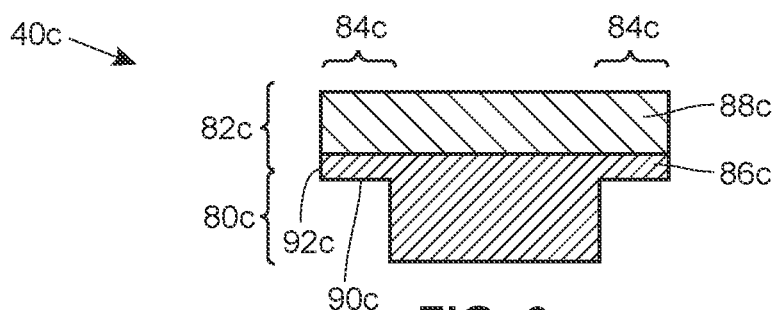
FIG. 6 is a cross-sectional view of yet another embodiment of a septum constructed in accordance with principles of the present disclosure.

Turning to FIG. 6, depicted is yet another embodiment of the septum 40c. Here, a portion of the distal end 82c of the septum 40c that is arranged distally relative to the flange 80c is made of the above-mentioned second material. Stated another way, the portion of the distal end 82c of the septum 40c that is arranged in the distal direction relative to an imaginary plane that is perpendicular to the longitudinal axis A and touches the distal end of the proximal end portion 86c of the flange 84c may be made of the second material. The remainder of the distal end 82c of the septum 40c, including the proximal end portion 86 of the flange 84 and a portion of the distal end 82c of the septum 40c located in the proximal direction relative to the above-mentioned imaginary plane, may be made of the above-mentioned first material. Also, in the present embodiment of the septum 40c, the proximal end 80c of the septum 40c may be made entirely of the first material. One benefit of the present embodiment of the septum 40c is that the gaseous sterilizing agent may be able to reach the inner surface 43 of the container 14 and sterilize any contaminants disposed thereon by diffusing through the proximal end 80c of the septum 40c.

Figure 7:
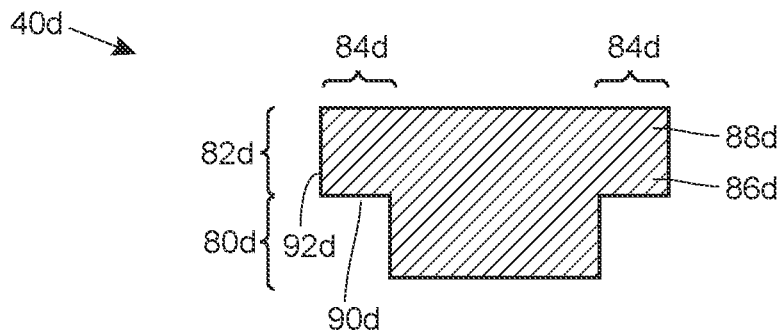
FIG. 7 is a cross-sectional view of still another embodiment of a septum constructed in accordance with principles of the present disclosure.

FIG. 7 illustrates another embodiment of the septum 40d, which is made entirely of the above-mentioned first material. As such, both the proximal and distal ends 80d and 82d of the septum 40d may be entirely of a material that is permeable to the gaseous sterilizing agent, including at least one of EtO or steam. This construction can help maximize the number diffusive pathways for the gaseous sterilizing agent. The gaseous sterilizing agent may be able to enter and exit the septum 40d through any exterior surface of the septum 40d. Accordingly, it may be possible to sterilize the interface between the flange 84d and the distal end surface 72 of the container 14, as well as the interface between the proximal end 80d of the septum 40d and the inner surface 43 of the container 14. Due to the relatively high permeability of the septum 40d, it may be beneficial to store the fully assembled drug delivery device 10 inside a sealed and/or sterile space of a bag or other secondary packaging prior to use. This may prevent any gases and/or contaminants from diffusing through the septum 40d in the period of time between assembly of the drug delivery device 10 and its use by a patient. In some embodiments, the secondary packaging may be may be constructed of a multilayer material having gas barrier properties. Moreover, any of the septa disclosed herein, including septa 40a, 40b, 40c, and 40d may be installed in a drug delivery device 10 that is subsequently placed within such secondary packaging, to provide additional protection against contamination in the period of time between assembly of the drug delivery device 10 and use by a patient.

The following description of the first material and the second material applies to any one of the above-described septa 40a, 40b, 40c, and 40d, and any other septum described herein. The composition of the first material may be chosen depending on any one of or any combination of the following non-exclusive list of characteristics of a sterilization procedure (e.g., a terminal sterilization procedure) used to sterilize the container 14 and/or other components of the drug delivery device 10: the composition of the gaseous sterilizing agent used in the sterilization procedure, the pressure of the gaseous sterilizing agent used in the sterilization procedure, the amount or volume of the gaseous sterilizing agent used in the sterilization procedure, the concentration of the gaseous sterilizing agent used in the sterilization procedure, the length of time of the sterilization procedure, and the temperature of the gaseous sterilizing agent used in the sterilization procedure. In some embodiments, the first material may be permeable to any one of or any combination of the gaseous sterilizing agents chosen from the following non-exclusive list of gaseous sterilizing agents: EtO, ozone, chlorine dioxide, nitrogen dioxide, and steam (e.g., pressurized water vapor). In some embodiments, the sterilization procedure utilizing steam as the gaseous sterilizing agent may be carried out within the interior of inside an autoclave device. The first material may include any one of or any combination of the following non-exclusive list of materials: a polymer, a rubber, and a polybutadiene rubber. The second material may include any one of or any combination of the following non-exclusive list of materials: a polymer, a rubber, a chlorobutyl rubber, and a halobutyl rubber. In any of the above-described septa 40a, 40b, 40c, and 40d, and any other septum described herein, the first material may be made of polybutadiene rubber, and the second material may be made of chlorobutyl rubber.

In general, the second material is less permeable to the gaseous sterilizing agent than the first material, which includes the second material being substantially or completely impermeable to the gaseous sterilizing agent. In some embodiments, the rate of permeation of the first material may be at least 10 times, or at least 20 times, or at least 30 times, or at least 40 times, or at least 50 times, or at least 60 times, or at least 70 times, or at least 80 times, or at least 90 times, or at least 100 times, greater than the rate of permeation of the second material.

Any one of the above-described septa 40a, 40b, 40c, and 40d, and any other septum described herein, may be constructed as one-piece component, where the first and second materials are integrally formed with each other, such as being injection molded with each other. Alternatively, any one of the above-described septa 40a, 40b, 40c, and 40d, and any other septum described herein, may be constructed as a multi-piece component, where the first material and the second material are connected to each other via an adhesive, a fastener(s), and/or any other suitable connecting element.

In embodiments where the fastener 94 is used hold the septum 40 against the container 14, the fastener ring 94 may act as a gas barrier that inhibits the gaseous sterilizing agent from diffusing through the permeable portion of the septum 40. Therefore, in some embodiments, one or more openings 99 (see FIG. 2B) may be formed in the fastener ring 94 to permit the gaseous sterilizing agent to pass through the fastener 94 and into contact with the permeable portion of the septum 40. In some embodiments, the openings 99 may be arranged in a pattern and/or formed in an outer peripheral or circumferential surface of the fastener 94. In some embodiments, the openings 99 may be located at the same axial position as the outer peripheral surface 92 of the proximal end portion 86 of the flange 84, as seen in FIG. 2B. In addition to the openings 99, or as an alternative to the openings 99, the fastener 94 may be partially or entirely constructed of a material that is permeable to the gaseous sterilizing agent (e.g., EtO, ozone, chlorine dioxide, nitrogen dioxide, and/or steam).

Figure 8:
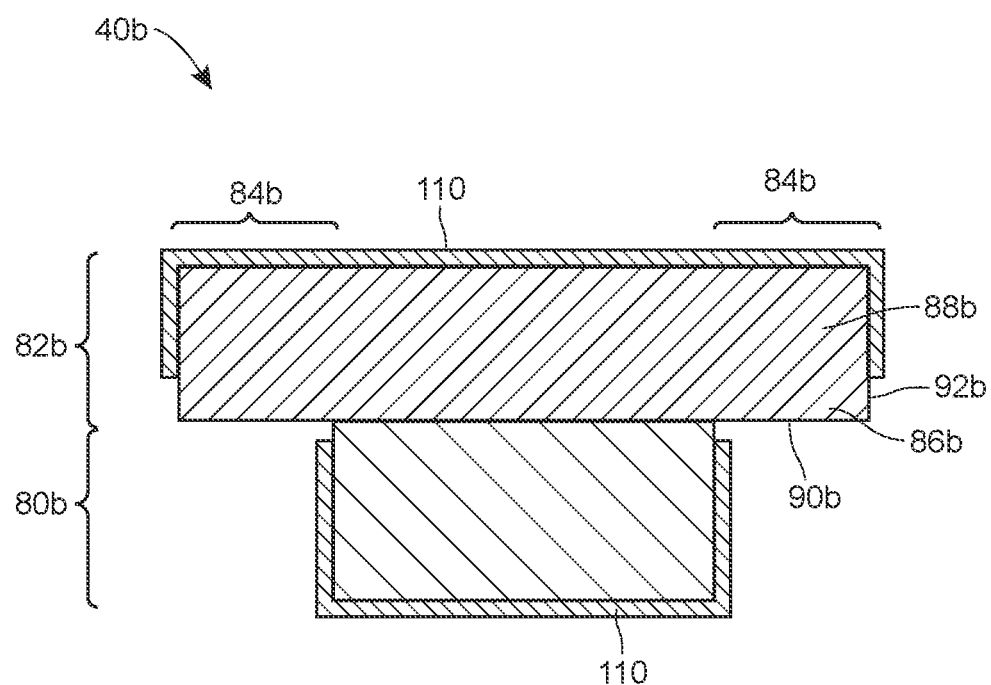
FIG. 8 is a partial cross-sectional view of the embodiment of the septum of FIG. 5, coated with a resin film.

Turning to FIG. 8, illustrated is an alternate version of the septum 40b, in which the exterior surface of the septum 40b is partially coated with a chemically inert resin film 110. In some embodiments, the resin film 110 may be a fluoropolymer film. With reference to FIGS. 5 and 8, the resin film 110 may cover the entire exterior surface of the septum 40b, except for the proximal end surface 90b and the outer peripheral surface 92b of the proximal end portion 86b of the flange 84b. As such, the resin film 110 may not inhibit the gaseous sterilizing agent from diffusing through the proximal end surface 90b and the outer peripheral surface 92b of the proximal end portion 86b of the flange 84b. In some embodiments, the portion of the resin film 110 covering the proximal end 80b and/or the distal end 82b of the septum 40b shown in FIG. 8 may be omitted. Also, any of the above-described configurations of the resin film 110 may be applied to any of the septa embodiments disclosed herein, including septa 40a, 40c, and 40d.

Figure 9A:
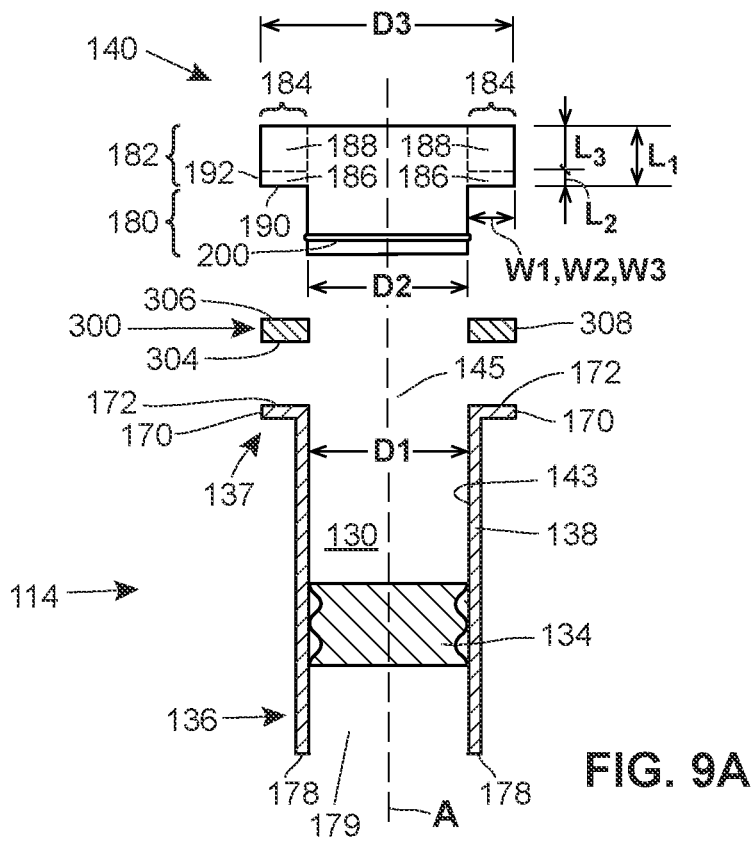
FIG. 9A depicts an exploded view of another embodiment of a container assembly, with a container, stopper, and ring-shaped sealing member being shown in cross-section.
Figure 9B:
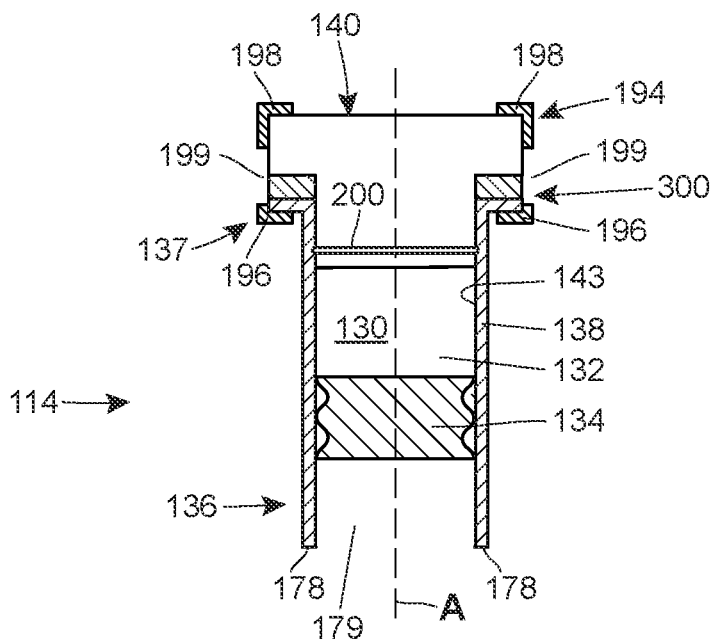
FIG. 9B illustrates an assembled view of the container assembly illustrated in FIG. 9A, with the container, the stopper, the ring-shaped sealing member, and the fastener being shown in cross-section.

Each of the foregoing embodiments relies on the septum to provide a diffusive pathway for the gaseous sterilizing agent. However, the diffusive pathway may be achieved by other means as well. FIGS. 9A and 9B illustrate an embodiment of the container assembly where the diffusive pathway is provided by a ring-shaped sealing member 300 or gasket which is separate from the septum 140. Elements of the container assembly depicted in FIGS. 9A and 9B which are similar to those shown in FIGS. 2A and 2B are designated by the same reference numeral, incremented by 100. A description of many of these elements is abbreviated or even eliminated in the interest of brevity.

Figure 10:
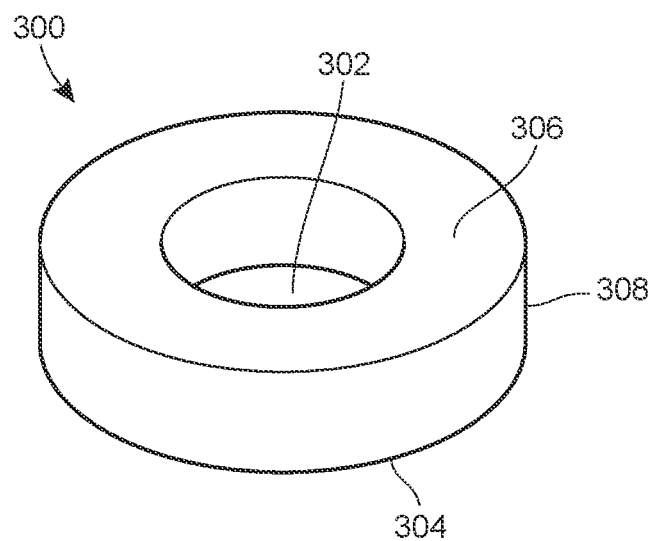
FIG. 10 is a top perspective view of the ring-shaped sealing member depicted in FIGS. 9A and 9B.

Referring to FIG. 9B, the ring-shaped sealing member 300, when assembled with the other components of the container assembly, is positioned between the proximal end surface 190 of the flange 184 and the distal end surface 172 of the container 114. As seen in FIG. 10, the ring-shaped sealing member 300 may include a central opening 302 extending between a proximal end surface 304 and a distal end surface 306. The proximal end 180 of the septum 140 may be inserted through the central opening 302 as seen in FIG. 9B. The ring-shaped sealing member 300 may also include an outer peripheral or circumferential surface 308 that extends between the proximal end surface 304 and the distal end surface 306.

During a sterilization procedure, the gaseous sterilizing agent may enter the ring-shaped sealing member 300 through the outer peripheral surface 308, diffuse through the material of the ring-shaped sealing member 300, and exit the ring-shaped sealing member 300 through the proximal end surface 304. Accordingly, any microbes or other contaminants attached at the interface between the ring-shaped sealing member 300 and the container 114 may be reduced or eliminated. The permeability of the ring-shaped sealing member 300 may be achieved by constructing the ring-shaped sealing member 300 of the first material described above. The foregoing description of the first material as incorporated into the septa 40a-d applies equally to the first material as incorporated into the ring-shaped sealing member 300.

With regard to the septum 140 which is used in combination with the ring-shaped sealing member 300, it may be constructed partially or entirely of a material which is less permeable to the gaseous sterilizing agent than the material used to construct the ring-shaped sealing member 300. In some embodiments, the septum 140 may be constructed partially or entirely of the second material describe above. In such embodiments, the foregoing description of the second material as incorporated into the septa 40a-c is applicable to the second material as incorporated into the septum 140. The ring-shaped sealing member 300 advantageously provides a diffusive pathway for the gaseous sterilizing agent to sterilize the distal end surface 172 of the container 114 should a conventional septum which is substantially or completely impermeable to the gaseous sterilizing agent be used to plug the container 114. Furthermore, the ring-shaped sealing member 300 is not limited for use with the septum 140; the ring-shaped sealing member 300 may be used in combination with any of the septa disclosed herein, including any of septa 40a-d.

Methods of assembling the drug delivery device 10 will now be described. Though the following description refers to the septum 40, it is applicable to all version of the septum disclosed herein, including at least septa 40a, 40b, 40,c, 40d, and 140. Initially, the empty container 14 and the septum 40 may be connected together and sterilized. This step may involve inserting the proximal end 80 of the septum 40 through the opening 45 into the interior volume 30 of the container 14, and moving the proximal end surface 90 of the flange 84 into direct contact with the distal end surface 72 of the container 14. In some embodiments, connecting the container 14 and the septum 40 may involve clamping the two components together with the fastener 94 to provide an air-tight and/or fluid-tight seal between the proximal end surface 90 of the flange 84 and the distal end surface 72 of the container 14. In embodiments where the ring-shaped sealing member 300 is included, the air-tight and/or fluid-tight seal may be created between the proximal end surface 304 of the ring-shaped sealing member 300 and the distal end surface 172 of the container 114, as well as between the distal end surface 306 of the ring-shaped sealing member 300 and the proximal end surface 190 of the septum 140.

Next, the partially-assembled container 14 may be subjected to a sterilization procedure or treatment. In some embodiments, this sterilization procedure may involve placing the partially-assembled container 14 in a sealed vacuum chamber that is subsequently filled with a gaseous sterilizing agent. The gaseous sterilizing agent may be any one of or any combination of the gaseous sterilizing agents chosen from the following non-exclusive list of gaseous sterilizing agents: EtO, ozone, chlorine dioxide, nitrogen dioxide, and steam (e.g., pressurized water vapor). In embodiments where steam is utilized for sterilization, the chamber in which the sterilization procedure is carried out may be an autoclave. During this sterilization procedure, the septum 40, and the ring-shaped sealing member 300 if it is included, may be exposed to the gaseous sterilizing agent. The portions of the septum 40 and/or the ring-shaped sealing member 300 constructed of the above-described first material may permit diffusion of the gaseous sterilizing agent such that the gaseous sterilizing agents diffuses through the septum 40 and/or the ring-shaped sealing member 300 and sterilizes the interface between the septum 40 or the ring-shaped sealing member 300 and the container 14, as described above. The period of exposure time for the gaseous sterilizing agent may be relatively short due to the effectiveness with which the gaseous sterilizing agent can diffuse through the septum 40 and/or the ring-shaped sealing member 300 and sterilize the interface at the container 14. In some embodiments, the period of exposure time for the gaseous sterilizing agent may be: less than or equal to approximately (e.g., ±10%) 24 hours, or 18 hours, or 12 hours, or 8 hours, or 4 hours, or 2 hours, or 1 hour; or within a range between approximately (e.g., ±10%) 1-4 hours, or 4-8 hours, or 4-12 hours, or 4-18, or 8-12 hours, or 8-18 hours, or 12-18 hours. The less time that the container 14 is exposed to the gaseous sterilizing agent, the less time that may needed for aeration of the container 14 following the sterilization procedure. Accordingly, the presently disclosed septum and ring-shaped sealing member may help streamline the manufacturing process of the container 14. In alternative embodiments, this step of sterilizing the partially-assembled container 14 may be omitted, or performed after the filling procedure described in the following paragraph.

Next, the container 14 and the septum 40 may be aseptically transferred to a filling and capping environment. Here, the interior volume 30 of the container 14 may be filled with the drug 32, and then the proximal end 36 of the container 14 may be sealed closed with the stopper 34, which is slidably inserted through the opening 79. This filling and capping environment may be operated as a sterile or aseptic assembly environment to ensure that microbes and other contaminants are not captured within the interior volume 30. Subsequently, this drug-filled, pre-assembled container assembly may be packaged and shipped to a facility where the final assembly of the drug delivery device 10 is to occur. Also, as a preliminary step, the fluid pathway assembly 22 may be connected to the seal member 60 such that the seal member 60 seals close an open end of the fluid passage 50. The process of assembling the fluid pathway assembly 22 and the seal member 60 may be performed in a sterile or aseptic assembly environment to ensure that particulate contaminants are not captured within the fluid passage 50. Alternatively or additionally, the pre-assembled arrangement of the fluid pathway assembly 22 and the seal member 60 may be subjected to high-energy sterilization beams (e.g., gamma ray beams, x-ray beams, electron beams, etc.), ethylene oxide, or other known techniques to ensure their sterility. This pre-assembled arrangement may then be packaged and shipped to a facility where the final assembly of the drug delivery device 10 is to occur.

Subsequently, at the final assembly facility for example, the drug-filled, pre-assembled arrangement of the drug container 14, septum 40, and stopper 34 and the pre-assembled arrangement of the fluid pathway assembly 22 and the seal member 60 may be installed within the housing 29 of the drug delivery device 10. In some embodiments, this installation process may involve: connecting the drug-filled, pre-assembled arrangement of the drug container 14, septum 40, and stopper 34 to a first housing portion (e.g., the bottom wall 25 of the housing 29) or a second housing portion (e.g., the top wall 27 of the housing 29) of the drug delivery device 10; and connecting the pre-assembled arrangement of the fluid pathway assembly 22 and the seal member 60 to the first housing portion or the second housing portion of the drug delivery device 10. In some embodiments, the installation of the drug-filled, pre-assembled arrangement of the drug container 14, septum 40, and stopper 34 within the housing 29 and/or other steps of the assembly the drug delivery device 10 may be carried out in a non-sterile or non-aseptic environment. In other embodiments, the installation of the drug-filled, pre-assembled arrangement of the drug container 14, septum 40, and stopper 34 within the housing 29 and some or all other steps of the assembly the drug delivery device 10 may be carried out in a sterile or aseptic environment.

After the drug-filled, pre-assembled arrangement of the drug container 14, septum 40, and stopper 34 and/or the pre-assembled arrangement of the fluid pathway assembly 22 and the seal member 60 have been installed within the housing 29, this partially-assembled version of the drug delivery device 10 may be subjected to a sterilization procedure or treatment. In some embodiments, this sterilization procedure may involve placing the partially-assembled version of the drug delivery device 10 in a sealed vacuum chamber that is subsequently filled with a gaseous sterilizing agent. The gaseous sterilizing agent may be any one of or any combination of the gaseous sterilizing agents chosen from the following non-exclusive list of gaseous sterilizing agents: EtO, ozone, chlorine dioxide, nitrogen dioxide, and steam (e.g., pressurized water vapor). In embodiments where steam is utilized for sterilization, the chamber in which the sterilization procedure is carried out may be an autoclave. During this sterilization procedure, the septum 40, and the ring-shaped sealing member 300 if it is included, may be exposed to the gaseous sterilizing agent. The portions of the septum 40 and/or the ring-shaped sealing member 300 constructed of the above-described first material may permit diffusion of the gaseous sterilizing agent such that the gaseous sterilizing agents diffuses through the septum 40 and/or the ring-shaped sealing member 300 and sterilizes the interface between the septum 40 or the ring-shaped sealing member 300 and the container 14, as described above. The period of exposure time for the gaseous sterilizing agent may be relatively short due to the effectiveness with which the gaseous sterilizing agent can diffuse through the septum 40 and/or the ring-shaped sealing member 300 and sterilize the interface at the container 14. In some embodiments, the period of exposure time for the gaseous sterilizing agent may be: less than or equal to approximately (e.g., ±10%) 24 hours, or 18 hours, or 12 hours, or 8 hours, or 4 hours, or 2 hours, or 1 hour; or within a range between approximately (e.g., ±10%) 1-4 hours, or 4-8 hours, or 4-12 hours, or 4-18, or 8-12 hours, or 8-18 hours, or 12-18 hours. The less time that the drug delivery device 10 is exposed to the gaseous sterilizing agent, the less time that may needed for aeration of the drug delivery device 10 following the sterilization procedure. Accordingly, the presently disclosed septum and ring-shaped sealing member may help streamline the manufacturing process of the drug delivery device 10.

After the sterilization procedure is complete, the first housing portion may be connected to the second housing portion to enclose the drug-filled, pre-assembled arrangement of the drug container 14, septum 40, and stopper 34 and/or other components (e.g., the insertion mechanism 12, the fluid pathway assembly 22, the drive mechanism 24, the controller 26, etc.) within a sterilized interior space of the drug delivery device 10. Accordingly, the enclosing step may result in a pre-loaded and pre-filled drug delivery device 10. In some embodiments, the connection between the first and second housing portions may seal the interior of the drug delivery 10 to prevent or inhibit the ingress of contaminants. Furthermore, in some embodiments, the first and second housing portions may be sealingly connected in the same environment or chamber in which the gaseous sterilization treatment was carried out.

It is noted that the foregoing method of assembly may be carried out with any of the above-described embodiments of the septum 40, including the septa 40a, 40b, 40c, 40d, and 140 and/or the ring-shaped sealing member 300.

EXAMPLE

Described below are the results an experimental test comparing a composite septum constructed in accordance with principles of the present disclosure relative to a conventional septum made entirely of a gas impermeable material. Both the composite septum and the conventional septum had the proximal end surface of their flange inoculated with approximately $10^{\wedge}6$ challenging microbes. Subsequently each septum was crimped against the distal end surface of a drug container. This process was repeated to create 30 samples utilizing the composite septum and 30 samples utilizing the conventional septum. Next, the samples were subjected to a gaseous sterilization treatment in which EtO was employed as the gaseous sterilizing agent. After 18 hours of EtO sterilization, no microbe growth was observed at the interface between the composite septum and the drug container in all 30 samples. Some composite septum samples exhibited no microbe growth after only 8 hours of EtO sterilization. By comparison, after 30 hours of EtO sterilization, only 15 of the 30 samples utilizing the conventional septum exhibited no microbe growth at the interface with the drug container. Accordingly, the amount of time needed to sterilize the interface between the presently disclosed composite septum and a container was empirically shown to be significantly less than that needed to sterilize the interface between a conventional septum and a container.

Drug Information

As mentioned above, the container may be filled with a drug. This drug may be any one or combination of the drugs listed below, with the caveat that the following list should neither be considered to be all inclusive nor limiting.

For example, the syringe may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the syringe may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications: U.S. Pat. Nos. 4,703,008; 5,441,868; 5,547,933; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858) as well as erythropoietin molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4;

Myostatin binding proteins, peptibodies, and related proteins, and the like, including myostatin specific peptibodies, particularly those described in U.S. Publication No. 2004/0181033 and PCT Publication No. WO 2004/058988, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1;

Interleukin 1-receptor 1 ("IL1-R1") specific antibodies, peptibodies, and related proteins, and the like, including but not limited to those described in U.S. Publication No. 2004/097712, pertinent to IL1-R1 specific binding proteins, monoclonal antibodies in particular, especially, without limitation, those designated therein: 15CA, 26F5, 27F2, 24E12, and 10H7;

Ang2 specific antibodies, peptibodies, and related proteins, and the like, including but not limited to those described in PCT Publication No. WO 03/057134 and U.S. Publication No. 2003/0229023, pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C1K; 2×L1C; Con4C; Con4C1K; 2×Con4C1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; Abl K, AbIP; and AbIP, in their various permutations as described therein;

NGF specific antibodies, peptibodies, and related proteins, and the like including, in particular, but not limited to those described in U.S. Publication No. 2005/0074821 and U.S. Pat. No. 6,919,426, particularly as to NGF-specific antibodies and related proteins in this regard, including in particular, but not limited to, the NGF-specific antibodies therein designated 4D4, 4G6, 6H9, 7H2, 14D10 and 14D11;

CD22 specific antibodies, peptibodies, and related proteins, and the like, such as those described in U.S. Pat. No. 5,789,554, as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein);

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, as to IL-15 specific antibodies and related proteins, including peptibodies, including particularly, for instance, but not limited to, HuMax IL-15 antibodies and related proteins, such as, for instance, 14687;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions as disclosed in the foregoing publication and in Thakur et al. (1999), Mol. Immunol. 36:1107-1115. In addition, description of the properties of these antibodies provided in the foregoing publication. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, as to TALL-1 binding proteins, particularly the molecules of Tables 4 and 5B;

Parathyroid hormone ("PTH") specific antibodies, peptibodies, and related proteins, and the like, such as those described in U.S. Pat. No. 6,756,480, particularly in parts pertinent to proteins that bind PTH;

Thrombopoietin receptor ("TPO-R") specific antibodies, peptibodies, and related proteins, and the like, such as those described in U.S. Pat. No. 6,835,809, particularly in parts pertinent to proteins that bind TPO-R;

Hepatocyte growth factor ("HGF") specific antibodies, peptibodies, and related proteins, and the like, including those that target the HGF/SF:cMet axis (HGF/SF: c-Met), such as the fully human monoclonal antibodies that neutralize hepatocyte growth factor/scatter (HGF/SF) described in U.S. Publication No. 2005/0118643 and PCT Publication No. WO 2005/017103, huL2G7 described in U.S. Pat. No. 7,220,410 and OA-5d5 described in U.S. Pat. Nos. 5,686,292 and 6,468,529 and in PCT Publication No. WO 96/38557, particularly in parts pertinent to proteins that bind HGF;

TRAIL-R2 specific antibodies, peptibodies, related proteins and the like, such as those described in U.S. Pat. No. 7,521,048, particularly in parts pertinent to proteins that bind TRAIL-R2;

Activin A specific antibodies, peptibodies, related proteins, and the like, including but not limited to those described in U.S. Publication No. 2009/0234106, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, particularly in parts pertinent to proteins that bind TGF-beta;

Amyloid-beta protein specific antibodies, peptibodies, related proteins, and the like, including but not limited to those described in PCT Publication No. WO 2006/081171, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No. 2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2013/048714, International Patent Application No. PCT/US2015/040211, International Patent Application No. PCT/US2015/056972, International Patent Application Publication No. WO/2008/057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the drug comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the drug comprises a therapeutically effective amount of the anti-TSLP antibody designated as A5 within U.S. Pat. No. 7,982,016.

While the present disclosure has been described in connection with various embodiments, it will be understood that the present disclosure is capable of further modifications. The present disclosure is intended to cover any variations, uses, or adaptations of the disclosed subject matter following, in general, the principles of the present disclosure, and including such departures from the present disclosure as, within the known and customary practice within the art to which the present disclosure pertains.

It is noted that the construction and arrangement of the drug delivery device and its various components and assemblies as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

What is claimed is:

1. A drug delivery device comprising:
   a housing;
   a container disposed in the housing and having an interior volume and an end surface, an opening being formed in the end surface and communicating with the interior volume;
   a drug disposed in the interior volume of the container;
   a septum including a proximal end and a distal end, the proximal end being inserted through the opening into the interior volume of the container, the distal end including a flange disposed outwardly of the proximal end and contacting the end surface of the container, an entirety of the septum being made of a material that is permeable to a gaseous sterilizing agent; and
   a resin film covering at least a portion of the exterior surface of the distal end of the septum, wherein the resin film does not cover the proximally facing surface of the flange.

2. The drug delivery device of claim 1, a proximally facing surface of the flange sealingly engaging the end surface of the container to inhibit the ingress of contaminants.

3. The drug delivery device of claim 1, the gaseous sterilizing agent including at least one of ethylene oxide or steam.

4. The drug delivery device of claim 1, wherein the resin film comprises a fluoropolymer film covering the septum entirely except for the proximally facing surface of the flange and a portion of an outer peripheral surface of the flange.

5. The drug delivery device of claim 1, wherein the material is permeable to at least ethylene oxide, ozone, chlorine dioxide, nitrogen dioxide, and/or steam.

6. A drug delivery device comprising:
- a housing;
- a container disposed in the housing and having an interior volume and an end surface, an opening being formed in the end surface and communicating with the interior volume;
- a drug disposed in the interior volume of the container;
- a septum including a proximal end and a distal end, the proximal end being inserted through the opening into the interior volume of the container, the distal end including a flange disposed outwardly of the proximal end and contacting the end surface of the container, an entirety of the septum being made of a material that is permeable to a gaseous sterilizing agent; and
- a fluoropolymer film covering the septum entirely except for the proximally facing surface of the flange and a portion of an outer peripheral surface of the flange.

* * * * *